(12) United States Patent
Van Gerwen

(10) Patent No.: US 9,071,910 B2
(45) Date of Patent: Jun. 30, 2015

(54) IMPLANTABLE MICROPHONE DEVICE

(75) Inventor: Peter Bart Jos Van Gerwen, Keerbergen (BE)

(73) Assignee: Cochlear Limited, Macquarie University, NSW (AU)

( * ) Notice: Subject to any disclaimer, the term of this patent is extended or adjusted under 35 U.S.C. 154(b) by 1131 days.

(21) Appl. No.: 13/055,620

(22) PCT Filed: Jul. 23, 2009

(86) PCT No.: PCT/AU2009/000935
§ 371 (c)(1),
(2), (4) Date: Apr. 11, 2011

(87) PCT Pub. No.: WO2010/009504
PCT Pub. Date: Jan. 28, 2010

(65) Prior Publication Data
US 2011/0178438 A1    Jul. 21, 2011

(30) Foreign Application Priority Data

Jul. 24, 2008  (AU) ................................ 2008903794

(51) Int. Cl.
*H04R 25/00* (2006.01)
*A61B 5/00* (2006.01)
*A61N 1/36* (2006.01)

(52) U.S. Cl.
CPC ............... *H04R 25/00* (2013.01); *A61B 5/6817* (2013.01); *A61N 1/36032* (2013.01); *H04R 2225/67* (2013.01)

(58) Field of Classification Search
CPC ..................... A61B 5/12; A61B 5/126; A61B 5/6815–5/6817; A61B 1/227; A61B 2018/00327; H04R 25/00; H04R 2225/67; H04R 1/222; A61N 1/36032
USPC ............................ 600/559, 587, 25; 623/10; 381/312–331, 364; 29/896.21
See application file for complete search history.

(56) References Cited

U.S. PATENT DOCUMENTS 3,963,881 A  *  6/1976  Fraim et al. ................... 381/357
4,596,902 A       6/1986  Gilman
4,868,799 A       9/1989  Massa (Continued)

FOREIGN PATENT DOCUMENTS

EP    0 751 695    1/1997
EP    1 434 464    6/2004

OTHER PUBLICATIONS

International Search Report for PCT/AU2009/000935, mailed Oct. 26, 2009, 4 pages.

*Primary Examiner* — Rene Towa
(74) *Attorney, Agent, or Firm* — Lowe Hauptman & Ham, LLP

(57) ABSTRACT

An implantable microphone device is provided. The device comprises a hermetically sealed housing (3) having an internal cavity (2). The internal cavity (2) has a microphone assembly arranged to receive sound waves originating from external the housing (3). The device further comprises a pressure sensor arrangement, arranged to detect and determine the differential pressure between the internal cavity (2) and the exterior of the housing (3). The determined differential pressure is used to determine a suitable transfer function to be applied to the output of the microphone assembly to produce a signal representative of the received sound waves.

15 Claims, 3 Drawing Sheets

(56) References Cited

U.S. PATENT DOCUMENTS

| | | | |
|---|---|---|---|
| 5,214,709 A * | 5/1993 | Ribic | 381/313 |
| 5,524,056 A * | 6/1996 | Killion et al. | 381/314 |
| 6,075,867 A * | 6/2000 | Bay et al. | 381/191 |
| 6,128,392 A | 10/2000 | Leysieffer et al. | |
| 6,422,991 B1 * | 7/2002 | Jaeger | 600/25 |
| 7,322,930 B2 | 1/2008 | Jaeger et al. | |
| 2003/0125602 A1 | 7/2003 | Sokolich et al. | |
| 2004/0019294 A1 | 1/2004 | Stirnemann | |
| 2005/0157895 A1 * | 7/2005 | Lichtblau | 381/312 |
| 2007/0009132 A1 | 1/2007 | Miller, III et al. | |
| 2009/0003621 A1 * | 1/2009 | Greywall | 381/92 |
| 2010/0329492 A1 * | 12/2010 | Derleth et al. | 381/317 |

* cited by examiner

IMPLANTABLE MICROPHONE DEVICE

CROSS-REFERENCE TO RELATED APPLICATION

The present application is a National Stage application of International Patent Application No. PCT/AU2009/000935, filed Jul. 23, 2009, and claims priority from Australian Patent Application No. 2008903794, filed Jul. 24, 2008. The contents of each of these applications is hereby incorporated by reference herein.

BACKGROUND

1. Field of the Invention

The present invention relates to an implantable microphone device, and in particular, to such a device suitable for use with an implanted hearing prosthesis.

2. Related Art

Hearing prostheses of various types are widely used to improve the lives of users. Such devices include, for example, hearing aids, cochlear implants, middle ear implants and electro-acoustic devices. A current trend is to develop totally implantable forms of these devices. Totally implantable devices have the advantage of allowing the user to have a superior aesthetic result, as the user is visually indistinguishable in day to day activities. They have a further advantage in generally being inherently waterproof, allowing the user to shower, swim, and so forth without needing to take any special measures.

Conventional hearing prostheses, for example partially implanted cochlear implant systems, use externally disposed microphones. To provide a totally implantable prosthesis a suitable implantable microphone needs to be employed. Replacing the external microphone assembly with a subcutaneous microphone assembly presents various practical difficulties. Principally, an implantable microphone assembly needs to be hermetically sealed.

The purpose of a microphone is to measure pressure variations in an audible frequency range. A conventional microphone includes a sound capturing membrane. To measure such pressure variations, the differential pressure between a side of the membrane, from where the sound originates, and the opposing reference side is measured. A conventional microphone also includes a purge hole disposed on the reference side of the membrane which exposes the reference side to outside ambient pressure. The purge hole is used to keep the ambient pressure on the reference side equal with the outside ambient pressure. The purge hole is necessary to compensate for any slow ambient pressure variations which could affect the measurement of differential pressure and hence the quality of the microphone output.

Given that an implantable microphone assembly needs to be hermetically sealed, it is clear that the use of such a purge hole cannot be employed.

In U.S. Pat. No. 7,322,930 there is disclosed an example of an implantable microphone device in which a microphone assembly is provided in a sealed cavity. The microphone assembly is provided with a flexible membrane which is intended to increase the sensitivity of the device. In practice, however, the quality of the microphone output has been found to be limited.

The issue of providing a microphone without an exterior purge hole is also encountered in hydrophones. U.S. Pat. No. 4,868,799 discloses an example of a hydrophone arrangement which deals with the issue by way of active pressure compensation. A valve operated mechanism increases the internal pressure to compensate for increasing external pressure depending upon the depth the hydrophone is submerged. While this may prove to be an effective solution where size of the device is not of concern, in respect of an implantable device such a bulky mechanism is impractical.

SUMMARY

According to the present invention there is provided an implantable microphone device, the device comprising a hermetically sealed housing having an internal cavity; the internal cavity having a microphone assembly arranged to receive sound waves originating from external the housing; the device further comprising a pressure sensor arrangement, arranged to detect and determine the differential pressure between said internal cavity and the exterior of said housing; wherein the determined differential pressure is used to determine a suitable transfer function to be applied to the output of said microphone assembly to produce a signal representative of said received sound waves.

In preferred embodiments, the pressure sensor arrangement comprises a differential pressure sensor. In alternative embodiments, the pressure sensor arrangement can comprise an internal pressure sensor, arranged to detect the pressure within the internal cavity, and an external pressure sensor arranged to detect the pressure external the housing; wherein the outputs of the internal and external pressure sensors are compared to determine the differential pressure.

Preferably, the microphone assembly comprises a microphone transducer and a cavity dividing membrane having an aperture; wherein the sound waves are received by the microphone transducer via said aperture. Ideally, the microphone assembly further comprises a microphone membrane disposed between the dividing membrane and the microphone transducer; the microphone membrane having a purge hole formed therethrough.

In preferred embodiments, the device further comprises a sealing membrane which seals the internal cavity from the exterior of the housing and allows the sound waves to pass therethrough.

According to exemplary embodiments, the internal cavity comprises a first and second cavity interconnected by a purge passage; the microphone assembly being arranged in the first cavity. When applicable, the internal pressure sensor may be arranged in the first and/or second cavity. The second cavity can house electronic components for the device.

The present invention advantageously provides an implantable microphone device which compensates for the necessary absence of a purge hole between the interior and exterior of the device.

BRIEF DESCRIPTION OF THE DRAWING

A preferred embodiment of the present invention will now be described with reference to the accompanying drawing, in which.

DETAILED DESCRIPTION

Figure 1:
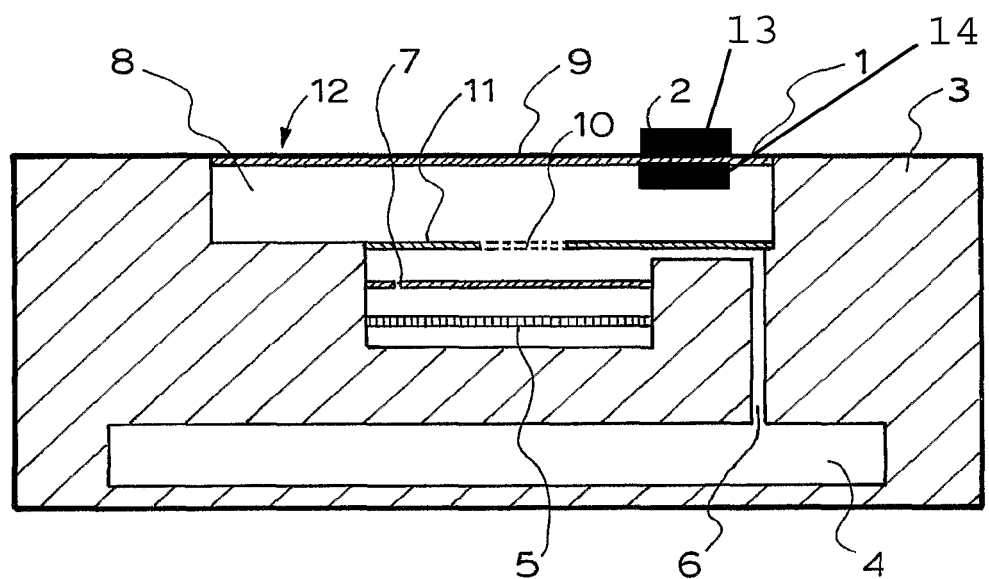
FIG. 1 is a cross-sectional view of an implantable microphone device.

Aspects of the present invention will be described with reference to a particular illustrative example. However, it will be appreciated that the present invention is applicable to any suitable hearing prosthesis system, for example a hybrid electrical/acoustic system, a cochlear implant system, an implantable hearing aid system, a middle ear stimulator or any other suitable hearing prosthesis. It may be applied to a system with totally implanted components, or to a system which additionally includes one or more external components. It will be appreciated that the present implementation is described for illustrative purposes, and its features are not intended to be limitative of the scope of the present invention. Many variations and additions are possible within the scope of the present invention.

As an underlying premise for an embodiment of the present invention, it is recognized that in practice a microphone is never perfect. A microphone translates received real sound pressure into an electrical signal. The relationship between the real sound pressure and the electrical signal would mathematically be defined by a transfer function. In other words, the transfer function describes the microphone output (e.g. how many volts) as a function of the sound input. For example, if a microphone 'hears' 60 dB SPL of sound at the input, how many microvolts is generated as output. Effectively by knowing the transfer function and measuring the generated electrical signal, the real sound pressure can be calculated or estimated.

Measuring and determining a transfer function for a microphone can be done in a soundbox, as will be familiar to the skilled person. A soundbox can be described as a closed box in which one can accurately and controllably generate sounds of certain characteristics and defined SPL. From this there are a number of known ways to calibrate the microphone. One way is by generating a sound of fixed frequency and measuring the voltage generated by the microphone. Repeating this for discrete steps over a range of frequencies allows the input/output relationship to be determined. The mathematical model of which relationship is the transfer function, which would be readily understood and derived by the skilled person.

With a calibrated microphone, by knowing the voltage output with a certain frequency and using the derived transfer function, the real input sound level can be deduced. In practice, the deduction calculation would be implemented by way of a look-up table.

The transfer function is affected by the ambient pressure and any ambient pressure differential across a microphone membrane. In an ordinary microphone device having a purge hole, the ambient pressure on each side of the membrane is equalized. This ambient pressure compensation negates any pressure difference and removes any effect on the transfer function. Hence, ordinarily the transfer function for a particular device can be derived during calibration of the device, as discussed above.

Figure 2:
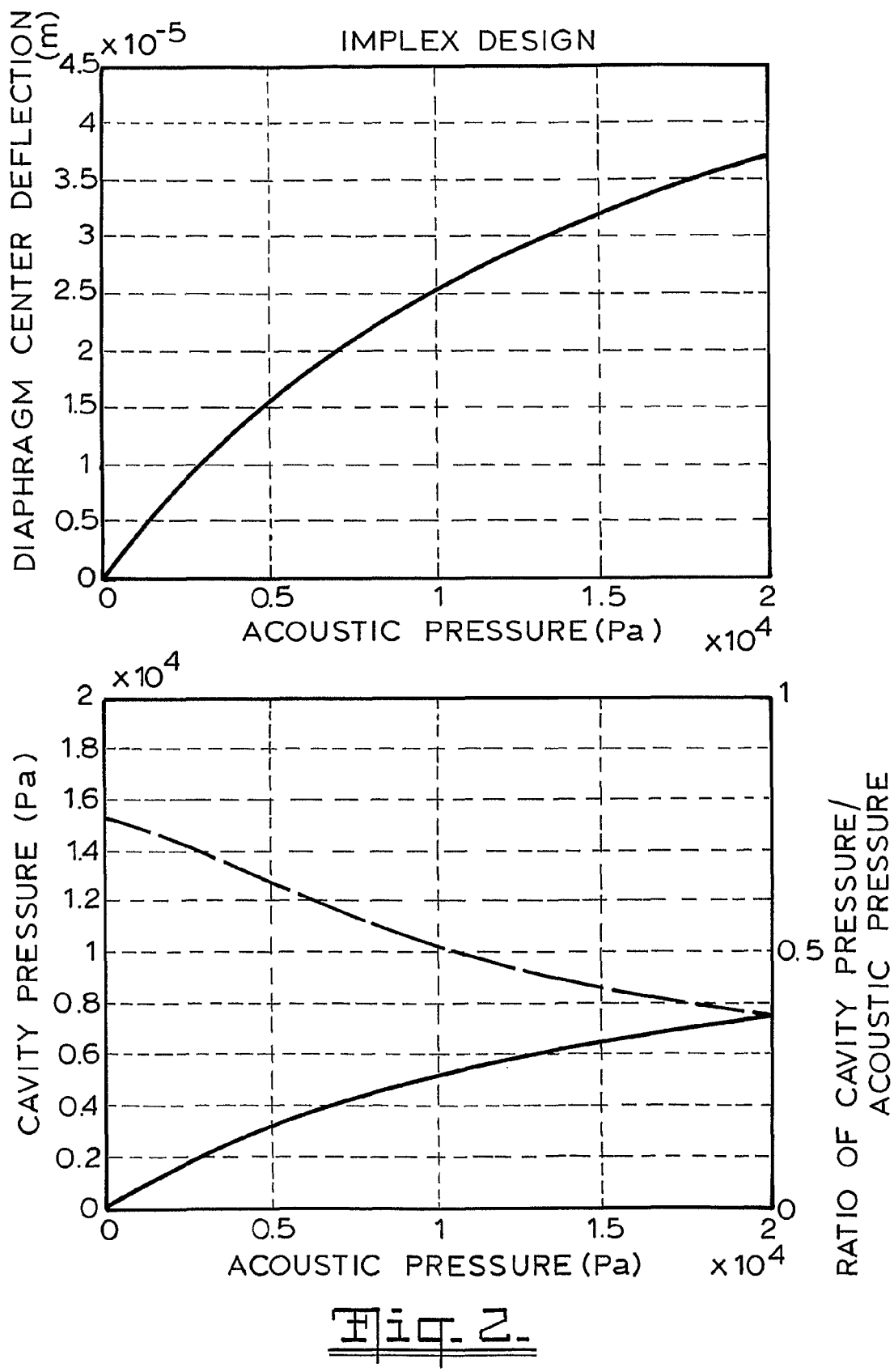
FIG. 2 shows plots demonstrating the effect of external pressure change on the output of an IMPLEX microphone.
Figure 3:
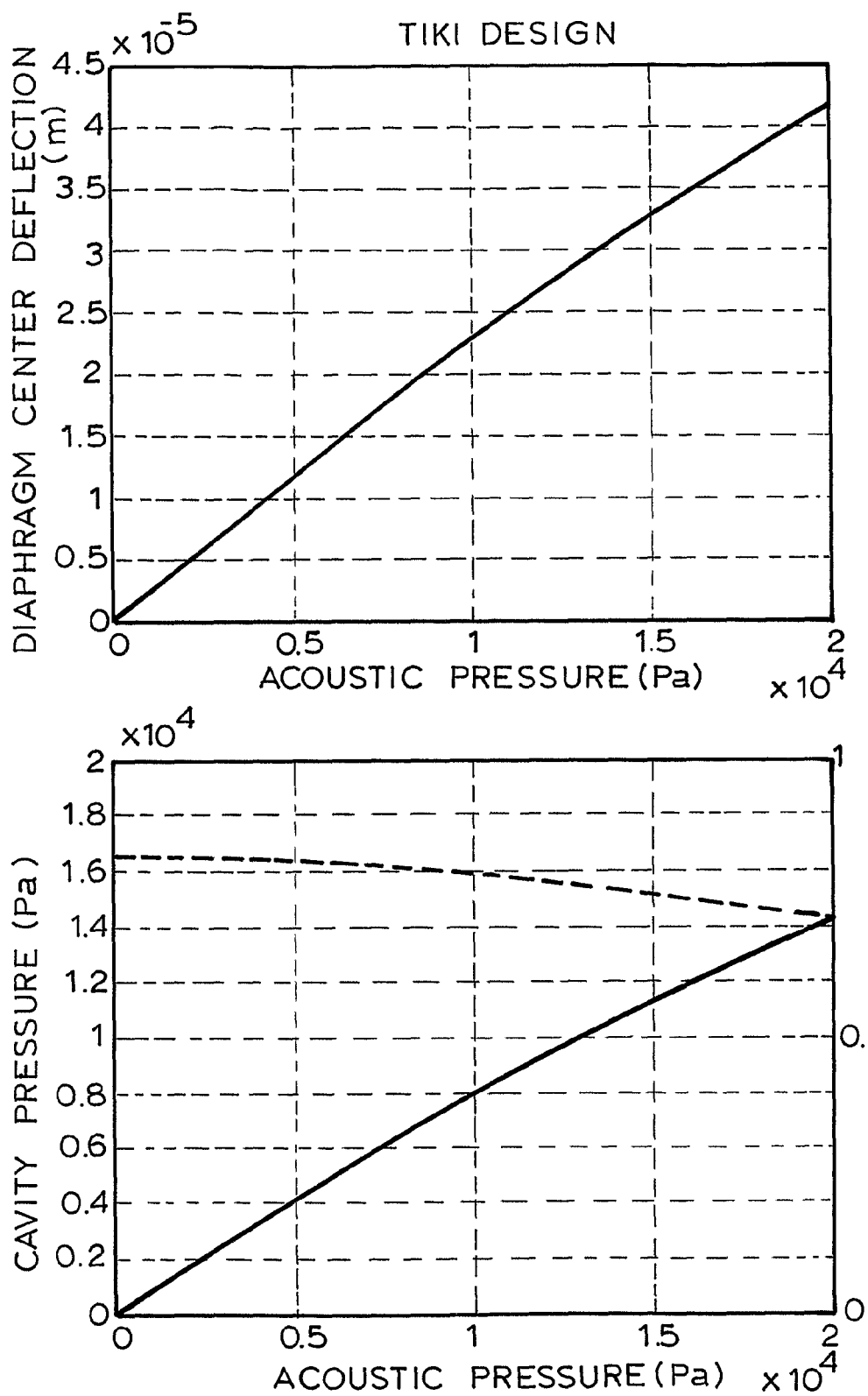
FIG. 3 shows plots demonstrating the effect of external pressure change on the output of a TKI microphone.

However, in a microphone device which cannot have a purge hole for equalizing ambient pressure across the microphone membrane, it has been recognized by the present inventor that variations in static and dynamic pressure difference inevitably has an effect on the transfer function. FIGS. 2 and 3 show plots of how external pressure changes affect microphone outputs for the TIKI and IMPLEX microphones. Such microphones are used in implantable devices. Implantable microphones are enclosed devices. If the outside pressure changes, the inner pressure cannot change due to the fact that the inside is hermetically sealed. Therefore, it is proposed that a device that can take the pressure difference into account would allow a better estimation for the transfer function and, hence, a better estimation of the actual sound pressure.

Examples, of such implantable microphones include the TIKI microphone and IMPLEX microphone.

In view of the above, in practice, if an external pressure difference occurs, the transfer function is consequently affected. Using the derived transfer function without taking the effect of the pressure change results in a loss of accuracy in determining actual sound pressure input.

The transfer function and the effect of pressure differential are derivable during an enhanced calibration of the device. For this purpose, a so-called pressure box is employed. A pressure box is a closed box in which one can accurately and controllably generate different ambient pressures. Combining the soundbox calibration method inside the pressure box allows for an enhanced calibration which would derive the transfer function for the microphone and derive how the transfer function is affected by the change in ambient pressure as controlled by the pressure box.

As an example, consider a hermetically sealed microphone with an internal pressure of 1 atmosphere (1013 mbar). The transfer function is calibrated as described before with the external pressure adjusted in discrete steps, for example in steps of 20 mbar. The outside pressure is changed in a range between, for example, 713 mbar and 1313 mbar, i.e. 31 steps with a pressure difference between −300 mbar and +300 mbar. For every pressure change a full transfer function is derived. It is expected that this enhanced calibration would be readily understood and be able to be implemented by the skilled person.

It is anticipated that an additional calibration technique could also allow for the adjustment of the internal pressure of the device and that further calibrated data could be derived based upon this additional parametric variation.

Based on the above, it is expected that the output of a properly calibrated device would allow for the input sound pressure to be calculated by relating the transfer function and the actual external pressure. In practice this calibration data would be provided in the form of look-up tables for use by a processor.

In FIG. 1, there is shown a structure for an implantable microphone device. The device includes a housing 3 having a primary internal cavity 2. The internal cavity 2 is hermetically sealed from the exterior of the housing 3 by a primary membrane 1, which allows sound waves to pass through from the exterior of the housing 3 into the primary cavity 2. The primary membrane 1 can be formed of biocompatible Titanium or other material suitable for implantable use. Arranged in the primary cavity 2 is a microphone assembly, illustrated as an electret microphone. The microphone assembly has microphone transducer in the form of a Mylar electret membrane 5 which outputs an electrical signal representative of detected pressure variations. A microphone membrane 7 having a purge hole formed therethrough is arranged in the path of the sound waves to the electret membrane 5. The purge hole provides internal ambient pressure compensation across the microphone membrane 7. A dividing membrane 11 having an aperture 10 is arranged between the microphone assembly and the primary membrane 1. The aperture 10 functions to focus received sound waves towards the centre of the microphone assembly.

The housing 3 also includes a secondary cavity 4, in which the various electronic components for the device, such as a printed circuit board, can be housed. The secondary cavity 4 is connected to the primary cavity 2 by a purge passage 6 which maintains an equalization of internal ambient pressure in the respective cavities 2, 4.

The device is provided with an external pressure sensor 13 arranged to detect and measure ambient pressure 12 external to the housing 3. In addition, one or more internal pressure sensors 14 are arranged within one or both of the primary and secondary cavities to detect and measure the internal ambient pressure 8. Arranging the internal pressure sensor 14 within the secondary cavity can prove convenient for its proximity with the electronics of the device.

A variety of different types of pressure sensors could be employed, such as: fibre optic sensors, mechanical deflection sensors, strain gauge, semiconductor peizoresistive, vibrating elements (silicon resonance, for example) and variable capacitance. Given the size constraints on an implantable device, it is considered that sensors based upon microelectromechanical systems (MEMS) are ideally suited, examples of which are:

Strain gauge—which measures the change in resistance experienced a material due to change in its stretch or strain due to pressure;

Semiconductor piezoresistive—which measures the change in conductivity of semiconductors due to change in pressure;

Vibrating elements (such as silicon resistance)—which measures the change in vibration on the molecular level of the different material elements due to change in pressure; and Variable capacitance—which measures the change of capacitance due to change of distance between the plates of a capacitor due to change in pressure.

This arrangement of external and internal pressure sensors allows the ambient pressure differential across the primary membrane 1 to be calculated. This pressure differential can be used by a processor and taken into account when determining and applying a suitable transfer function to the electrical signal output from the microphone in order to generate a signal representative of the received sound. The generated signal can be used in the processing of suitable stimulation signals for a hearing prosthesis, such as a cochlear implant system.

As an alternative to having separate internal and external pressure sensors, a more convenient arrangement is to use a single differential pressure sensor, which outputs a differential pressure signal rather than having to calculate differential pressure from the difference between two measured signals. The variable capacitance-type sensor is readily suitable for this purpose, whereby a first plate of the sensor 13 can be arranged within the primary membrane 1 and the second plate 14 could be arranged within the internal cavity, for example with the dividing membrane 11 or the adjacent wall.

While the present invention has been described with respect to a specific embodiment, it will be appreciated that various modifications and changes could be made without departing from the scope of the invention.

The invention claimed is:

1. An implantable microphone device, said device comprising:
   a hermetically sealed housing having an internal cavity; said internal cavity having a microphone assembly arranged to receive sound waves originating external from said housing; and
   a pressure sensor arrangement, arranged to detect and determine a differential pressure between said internal cavity and an exterior of said housing; wherein the determined differential pressure is used by a processor coupled to the device to determine a suitable transfer function to be applied to an output of said microphone assembly to produce a signal representative of said received sound waves, wherein the pressure sensor arrangement comprises:
   an internal pressure sensor, arranged to detect a pressure within said internal cavity; and
   an external pressure sensor arranged to detect a pressure external said housing;
   wherein the outputs of the internal and the external pressure sensors are to be compared to determine the differential pressure.

2. The implantable microphone device according to claim 1, wherein said pressure sensor arrangement comprises a differential pressure sensor.

3. The implantable microphone device according to claim 1, wherein said microphone assembly comprises a microphone transducer and a cavity dividing membrane having an aperture; wherein said microphone transducer is configured to receive said sound waves via said aperture.

4. The implantable microphone device according to claim 3, wherein said microphone assembly further comprises a microphone membrane disposed between said cavity dividing membrane and said microphone transducer; said microphone membrane having a purge hole formed therethrough.

5. The implantable microphone device according to claim 1, further comprising a sealing membrane that seals said internal cavity from the exterior of said housing and allows said sound waves to pass therethrough.

6. The implantable microphone device according to claim 1, wherein said internal cavity comprises a first and second cavity interconnected by a purge passage; said microphone assembly being arranged in said first cavity.

7. The implantable microphone device according to claim 6, wherein said internal pressure sensor is arranged in said first and/or second cavity.

8. The implantable microphone device according to claim 6, wherein said second cavity houses electronic components for said device.

9. An implantable hearing prosthesis system including an implantable microphone device, said implantable microphone device comprising:
   a hermetically sealed housing having an internal cavity; said internal cavity having a microphone assembly arranged to receive sound waves originating from external said housing; and
   a pressure sensor arrangement, arranged to detect and determine the differential pressure between said internal cavity and an exterior of said housing; wherein the system includes a processor that is configured to use the determined differential pressure to determine a suitable transfer function to be applied to an output of said microphone assembly to produce a signal representative of said received sound waves,
   wherein the pressure sensor arrangement comprises:
   an internal pressure sensor, arranged to detect a pressure within the internal cavity; and
   an external pressure sensor arranged to detect a pressure external the housing;
   wherein the system is configured to compare the outputs of the internal and the external pressure sensors to determine the differential pressure.

10. The implantable hearing prosthesis system of claim 9, wherein said system is a cochlear implant system.

11. The implantable hearing prosthesis system of claim 9, wherein said pressure sensor arrangement comprises a differential pressure sensor.

12. The implantable hearing prosthesis system of claim 9, wherein said microphone assembly comprises a microphone transducer and a cavity dividing membrane having an aperture; wherein said microphone transducer is configured to receive said sound waves via said aperture.

13. The implantable hearing prosthesis system according to claim 12, wherein said microphone assembly further comprises a microphone membrane disposed between said cavity dividing membrane and said microphone transducer; said microphone membrane having a purge hole formed therethrough.

14. The implantable hearing prosthesis system of claim 9, further comprising a sealing membrane which seals said internal cavity from the exterior of said housing and allows said sound waves to pass therethrough.

15. An implantable hearing prosthesis system including an implantable microphone device, said implantable microphone device comprising:
   a hermetically sealed housing having an internal cavity; said internal cavity having a microphone assembly arranged to receive sound waves originating from external said housing; and
   a pressure sensor arrangement, arranged to detect and determine the differential pressure between said internal cavity and an exterior of said housing; wherein the system includes a processor that is configured to use the determined differential pressure to determine a suitable transfer function to be applied to an output of said microphone assembly to produce a signal representative of said received sound waves,
wherein said internal cavity comprises a first and second cavity interconnected by a purge passage; said microphone assembly being arranged in said first cavity, and
wherein said system is configured to compare the outputs of said internal and external pressure sensors to determine said differential pressure; and wherein said internal pressure sensor is arranged in said first and/or second cavity.

* * * * *